United States Patent
Kim et al.

(10) Patent No.: US 8,915,873 B2
(45) Date of Patent: Dec. 23, 2014

(54) KNEE BRACE WITH A RECIPROCAL HINGE

(75) Inventors: Cheol Woong Kim, Seoul (KR); Jung Heum Yoon, Seoul (KR); Young Gyu Yang, Seoul (KR); Min Hyung Park, Seoul (KR); Hye Min Park, Gyeonggi-do (KR)

(73) Assignee: Triple-C Medical Corporation, Seoul (KR)

( * ) Notice: Subject to any disclaimer, the term of this patent is extended or adjusted under 35 U.S.C. 154(b) by 83 days.

(21) Appl. No.: 13/391,255

(22) PCT Filed: Jul. 5, 2010

(86) PCT No.: PCT/KR2010/004345
§ 371 (c)(1),
(2), (4) Date: Feb. 17, 2012

(87) PCT Pub. No.: WO2011/201772
PCT Pub. Date: Feb. 24, 2011

(65) Prior Publication Data
US 2012/0150084 A1    Jun. 14, 2012

(30) Foreign Application Priority Data

Aug. 18, 2009   (KR) .................. 10-2009-0076231

(51) Int. Cl.
*A61F 5/00* (2006.01)
*A61F 5/01* (2006.01)

(52) U.S. Cl.
CPC ....... *A61F 5/0123* (2013.01); *A61F 2005/0148* (2013.01); *A61F 2005/0165* (2013.01)
USPC ................ 602/16; 602/23; 602/26

(58) Field of Classification Search
USPC ................ 602/16, 23, 26, 5, 20, 27
See application file for complete search history.

(56) References Cited

U.S. PATENT DOCUMENTS

| 5,005,565 A | 4/1991 | Fratesi |
| 5,009,223 A | 4/1991 | DeFonce |

(Continued)

FOREIGN PATENT DOCUMENTS

KR    10-0834074 B1    6/2008

OTHER PUBLICATIONS

English Language Abstract of KR 10-0834074 B1.

(Continued)

*Primary Examiner* — Patricia Bianco
*Assistant Examiner* — Keri J Nelson
(74) *Attorney, Agent, or Firm* — Rabin & Berdo, P.C.

(57) ABSTRACT

According to one embodiment of the present invention, a knee brace comprises: an upper brace positioned at a thigh region of a wearer when the knee brace is worn; a lower brace positioned at a shin region of the wearer when the knee brace is worn; and a reciprocal hinge connecting the upper brace to the lower brace such that the lower brace is rotatable with respect to the upper brace. The reciprocal hinge includes: a guide plate connected to either the upper brace or the lower brace, and having a first and a second guide hole intersecting one another and forming a preset angle; a first and a second moving body which move along the first and second guide holes, respectively; and a connecting bar, one end of which is connected to either the upper brace or the lower brace and the other end of which is rotatably coupled to the first and second moving bodies, such that the connecting bar is rotated with respect to the guide plate according to the movement of the first and second moving bodies along the first and second guide holes, respectively.

8 Claims, 11 Drawing Sheets

(56) References Cited

U.S. PATENT DOCUMENTS

| | | |
|---|---|---|
| 5,107,823 A | 4/1992 | Fratesi |
| 5,107,824 A | 4/1992 | Rogers et al. |
| 5,230,696 A | 7/1993 | Silver et al. |
| 5,997,493 A * | 12/1999 | Young .............................. 602/16 |
| 2009/0182254 A1 | 7/2009 | Cho |

OTHER PUBLICATIONS

International Search Report of PCT/KR2010/004345 mailed on Mar. 14, 2011.

* cited by examiner

KNEE BRACE WITH A RECIPROCAL HINGE

TECHNICAL FIELD

The present invention relates to a knee brace, and more particularly, to a knee brace with a reciprocal hinge.

BACKGROUND ART

Knee joints are joints which are positioned at a lower end of the thighbone, an upper end of the shinbone, and a rear side of the kneecap (i.e., the patella) to adjust a refraction angle and an extension angle between the thighbone and the shinbone. When a knee is extended, the collateral ligament is tensed, and the lower leg may be disposed linearly with respect to the thigh. On the other hand, when the knee is bent, the lower leg may be extended to allow the lower leg to be moved somewhat in left and right directions.

In general, when a knee is injured such as a damage of the kneecap or an injury of the ligament or osteoarthritis due to aging occurs, knee braces may fix and protect a knee joint region and limit a refraction angle and an extension angle of the knee to prevent a lesion from being progressed (e.g., a collateral damage of the ligament or muscle), thereby smoothly treating diseases. Thus, such a knee brace should be designed so that a motion radius (or a rotation radius) of the knee brace approaches an actual motion radius of a knee joint. Here, a difference between the motion radius of the knee brace and the actual motion radius of the knee joint may cause a collateral injury of wearer. Also, since the wearer can feel easefulness according to the approaching degree, the motion radius of the knee brace may be very important.

DISCLOSURE OF THE INVENTION

Technical Problem

An object of the present invention is to provide a knee brace which realizes a motion similar to a rotation motion of a knee joint.

Another object of the present invention is to provide a knee brace which protects a knee joint of a wearer.

Further another object of the present invention will become evident with reference to following detailed descriptions and accompanying drawings.

Technical Solution

In one embodiment, a knee brace includes: an upper brace disposed to correspond to a thigh region of a wearer when the knee brace is worn; a lower brace disposed to correspond to a shin region of the wearer when the knee brace is worn; and a reciprocal hinge connecting the upper brace to the lower brace so that the lower brace is relatively rotated with respect to the upper brace, wherein the reciprocal hinge includes: a guide plate connected to one of the upper brace and the lower brace, the guide plate having first and second guide holes crossing each other to define a preset angle; first and second moving bodies respectively moved along the first and second guide holes; and a connecting bar having one end connected to one of the upper brace and the lower brace and the other end rotatably connected to the first and second moving bodies, the connecting bar being rotated with respect to the guide plate as the first and second moving bodies are moved along the first and second guide holes, respectively.

The first and second guide holes may be perpendicular to each other.

The one end of the connection bar may be rotated along an elliptical orbit when the connection bar is rotated.

The reciprocal hinge may have a rotation angle, and the rotation angle may be an angle defined by the connection bar when the first moving body is disposed on one end of the guide hole and the second moving body is disposed on one end of the second guide hole and when the connection bar and the first moving body are disposed on the other end of the first guide hole and the second moving body is disposed on the other end of the second guide hole.

The reciprocal hinge may further include a stopper inserted into one of the first and guide holes to restrict the movement of one of the first and second moving bodies.

The reciprocal hinge may further include a damper connected to a rear end of the stopper to absorb an impact applied to the stopper.

The connecting bar may be connected to the first and second moving bodies by first and second coupling members, respectively, and the connecting bar may be rotated with respect to centers of the first and second coupling members, respectively.

In another embodiment, a knee brace includes: an upper brace disposed to correspond to a thigh region of a wearer when the knee brace is worn; a lower brace disposed to correspond to a shin region of the wearer when the knee brace is worn; and a reciprocal hinge connecting the upper brace to the lower brace so that the lower brace is relatively rotated with respect to the upper brace, wherein the reciprocal hinge includes: a guide plate connected to the upper brace, the guide plate having first and second guide holes crossing each other to define a preset angle; first and second moving bodies respectively moved along the first and second guide holes; and a connecting bar having one end connected to the lower brace and the other end rotatably connected to the first and second moving bodies, the connecting bar being rotated with respect to the guide plate as the first and second moving bodies are moved along the first and second guide holes, respectively, wherein the first guide hole extends in front and rear directions of the thigh region and is inclined upward toward a rear side, and the second guide hole extends in a vertical direction of the thigh region and is substantially perpendicular to the first guide hole.

The first guide hole may have a first front guide hole defined in a front side of the second guide hole and a first rear guide hole defined in a rear side of the second guide hole, and the first front guide hole may have a length less than that of the first rear guide hole.

Advantageous Effects

According to the present invention, the motion of the knee brace may be realized similar to the rotation motion of the knee joint, and also, the knee brace may protect the knee joint of the wearer against external impacts.

MODE FOR CARRYING OUT THE INVENTION

Figure 1:
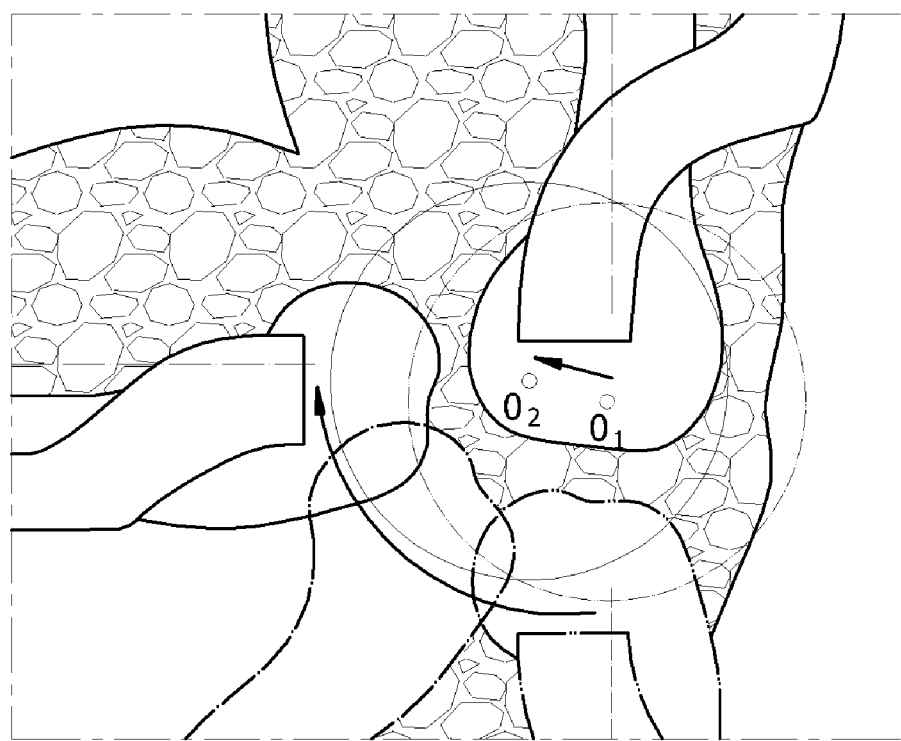
FIG. 1 is a photograph illustrating an actual motion occurring when a knee joint is bent.

Hereinafter, preferred embodiments will be described in more detail with reference to FIGS. 1 to 11. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Thus, in the drawings, the shapes and sizes of elements are exaggerated for clarity.

Also, the terms "movement", "rotation", and "angle switching" that will be described below may be used as "relative" meanings. For example, a meaning that an "A" is moved with respect to a "B" may denote that the "A" is moved in a state where the "B" is fixed and that the "B" is moved in a state where the "A" is fixed. Also, terms "upper", "lower", "left", "right", "front", and "rear" have only "relative" meanings. Thus, the meanings of the terms "upper", "lower", "left", "right", "front", and "rear" may be varied according to a setting method of coordinates with respect to structures.

FIG. 1 is a photograph illustrating an actual motion occurring when a knee joint is bent. As described above, knee joints are joints which are positioned at a lower end of the thighbone, an upper end of the shinbone, and a rear side of the kneecap (i.e., the patella) to adjust a refraction angle and an extension angle between the thighbone and the shinbone by a desired angle. Referring to FIG. 1, when a knee is bent, the upper end of the shinbone is rotated with respect to a center of the lower end of the thighbone. Here, the upper end of the shinbone has a rotation center moved from $O_1$ to $O_2$.

That is, when the upper end of the shinbone is disposed at the lower end of the thighbone, a rotation center of the upper end of the shinbone may be defined at $O_1$. Then, when the knee is bent, the upper end of the shinbone is slidably moved along the lower end of the thighbone, and thus a rotation center of the upper end of the shinbone may be defined at $O_2$. Thus, as shown in FIG. 1, the rotation center of the upper end of the shinbone may be moved ($O_1 \rightarrow O_2$). That is, the upper end of the shinbone may be moved along an elliptical orbit.

Figure 2:
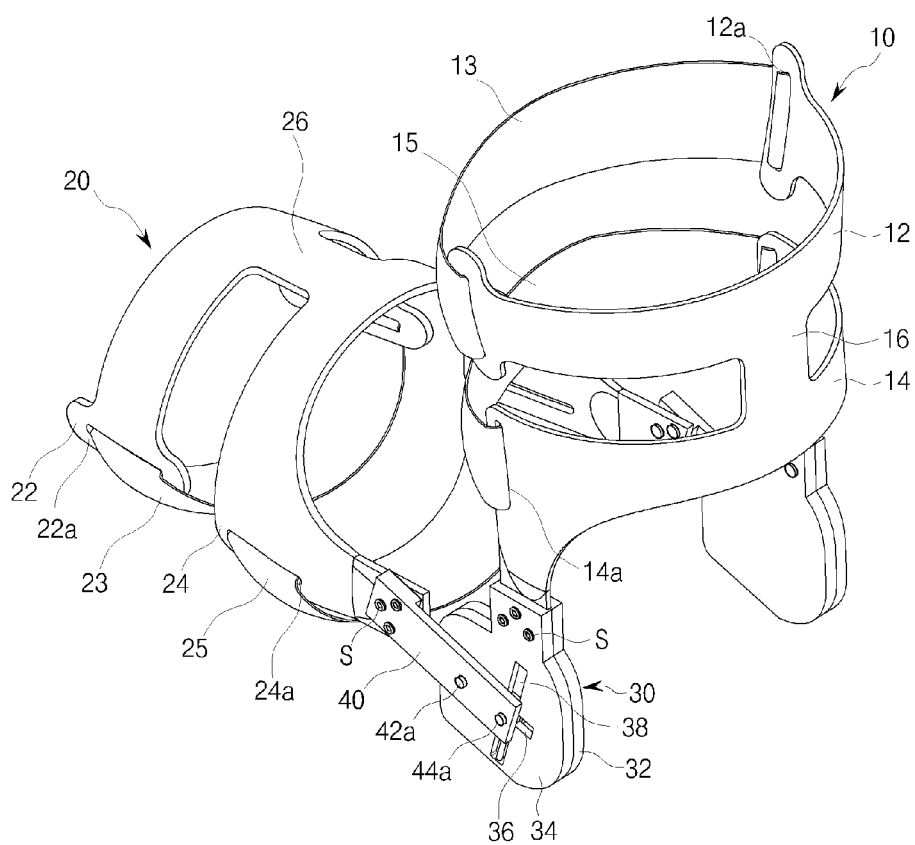
FIG. 2 is a schematic view of a knee brace according to an embodiment of the present invention.
Figure 3:
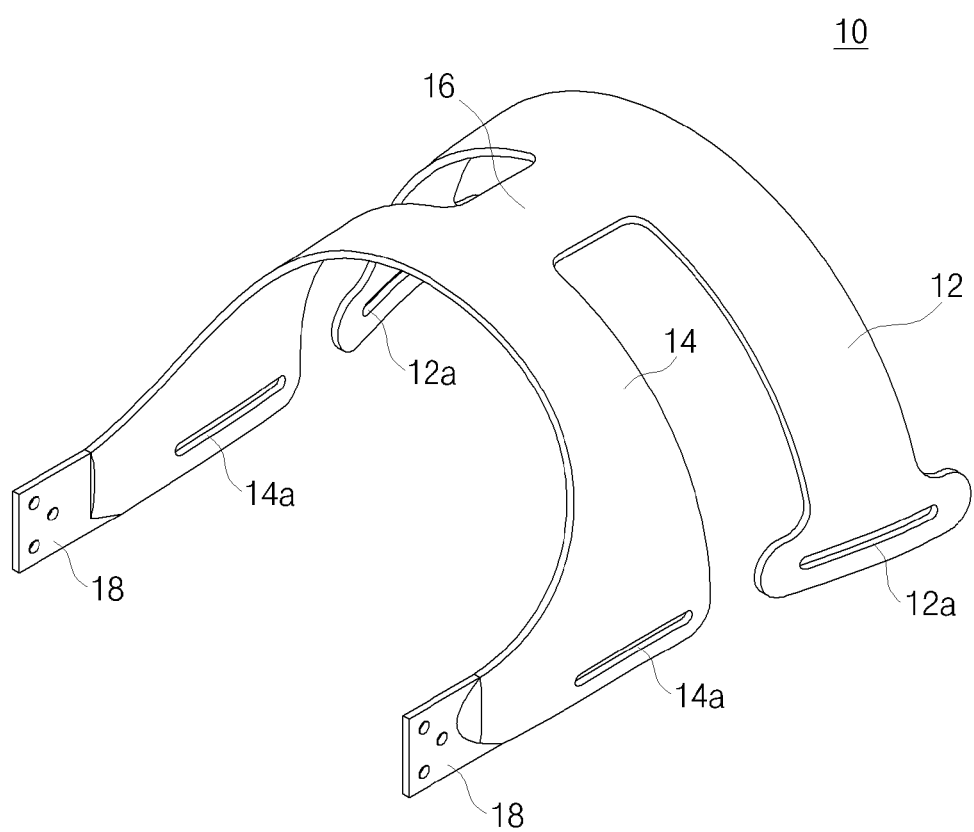
FIG. 3 is a view illustrating an upper brace of FIG. 2.
Figure 4:
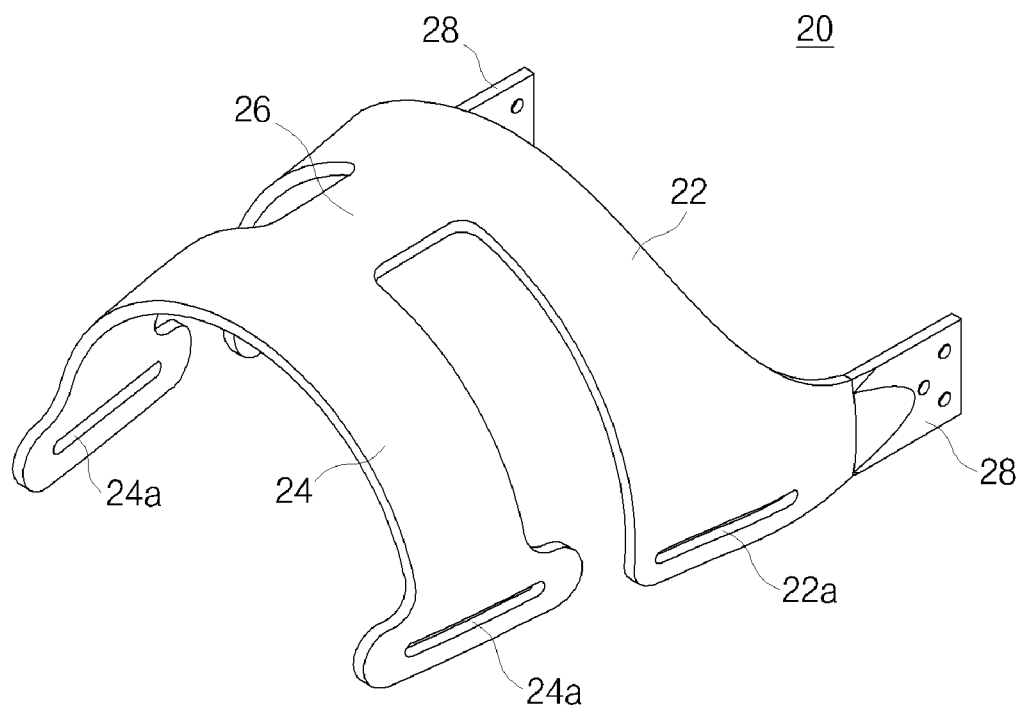
FIG. 4 is a view illustrating a lower brace of FIG. 2.

FIG. 2 is a schematic view of a knee brace according to an embodiment of the present invention. FIG. 3 is a view illustrating an upper brace of FIG. 2. FIG. 4 is a view illustrating a lower brace of FIG. 2.

A knee brace includes an upper brace 10, a lower brace 20, a reciprocal hinge 30, and a connecting bar 40. A wearer wears the knee brace, the upper brace 10 is fixed to a tight region of the wearer, and the lower brace 20 is fixed to a shin region of the wearer. When the wearer's knee is bent, the shin region of the wearer is rotated and moved with respect to the tight region, and the lower brace 20 is rotated and moved with the upper brace 10 together with the shin region of the wearer. The upper brace 10 and the lower brace 20 are relatively rotatable with respect to each other. Also, since the upper brace 10 and the lower brace 20 are relatively disposed at front and rear positions, the upper brace 10 and the lower brace which will be described below may be changed in structure and function with respect to each other.

Referring to FIG. 3, the upper brace 10 (or an anterior thighstrap (AST)) includes upper straps 12 and 14 which are spaced from each other and disposed parallel to each other. The upper straps 12 and 14 are disposed on a front surface of the tight region to surround the front surface of the tight region. Here, each of the upper straps 12 and 14 may be formed of a hard material (for example, a metal, polymer, or CFRP).

The upper straps 12 and 14 have upper band holes 12*a* and 14*a* in which upper bands 13 and 15 are inserted. For example, the upper band 13 presses a rear surface of the tight region formed of an elastic material to firmly fix the upper brace 10 to the tight region in a state where the upper band 13 is fitted into the upper band hole 12*a*. The upper straps 12 and 14 are connected to each other through a connecting strap 16. An upper fixing bar 18 is connected to a lower portion of the upper strap 14. Also, as shown in FIG. 2, the upper fixing bar 18 is connected to the reciprocal hinge 30 that will be described later in detail through a coupling member such as a screw S (or a rivet).

Referring to FIG. 4, the lower brace 20 (or a calf band) includes lower straps 22 and 24 which are spaced from each other and disposed parallel to each other. The lower straps 22 and 24 are disposed on a rear surface (e.g., a calf region) of the shin region to surround the rear surface of the shin region. Here, each of the lower straps 22 and 24 may be formed of an extendable band material having elasticity (for example, a chamois pneumatic strap). Thus, expansion of the calf muscle may be allowable to improve wear sensation.

The lower straps 22 and 24 have lower band holes 22*a* and 24*a* in which lower bands 23 and 25 are inserted. For example, the lower band 23 presses a rear surface of the shin region formed of an elastic material to firmly fix the lower brace 20 to the shin region in a state where the lower band 23 is fitted into the lower band hole 22*a*. The lower straps 22 and 24 are connected to each other through a connecting strap 26. A lower fixing bar 28 is connected to an upper portion of the lower band 22. Also, as shown in FIG. 2, the lower fixing bar 28 is connected to the connecting bar 40 through a coupling member such as a screw S (or a rivet).

Figure 5:
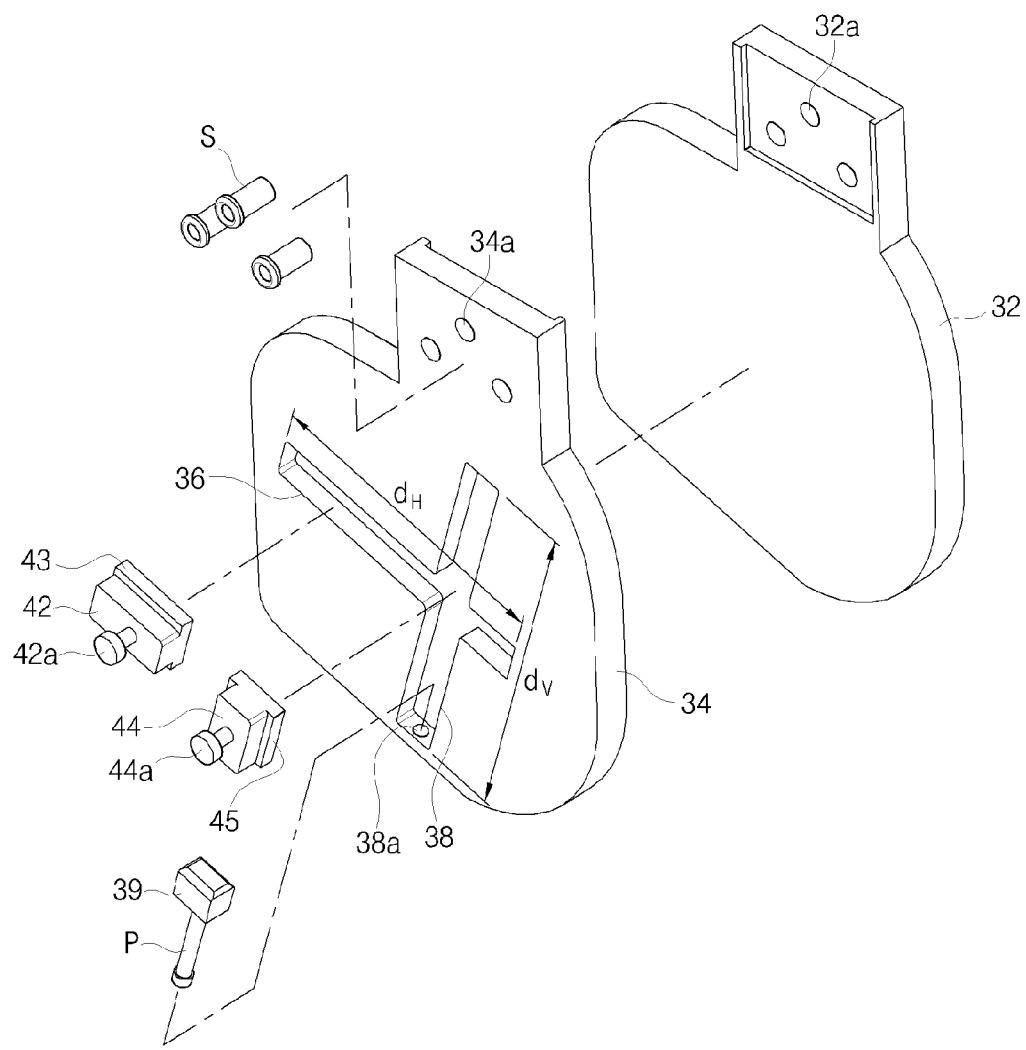
FIG. 5 is a view illustrating a reciprocal hinge of FIG. 2.

FIG. 5 is a view illustrating the reciprocal hinge 30 of FIG. 2. The reciprocal hinge 30 includes a base plate 32 and a guide plate 34. The base plate 32 and the guide plate 34 have shapes corresponding to each other. The guide plate 34 is coupled to the base plate 32 through a coupling member such as a screw S (on the other hand, the guide plate 34 may be coupled to the base plate 32 through welding). The screw S passes through a through hole 34*a* defined in the guide plate 34 and is coupled to a coupling hole 32*a* defined in the base plate 32. Unlike the current embodiment, the guide plate 34 may be rotatably connected to the base plate 32. Thus, a horizontal guide hole 36 and a vertical guide hole 38 which will be described later may be adjusted in position.

The guide plate 34 has the horizontal guide hole 36 and the vertical guide hole 38. The horizontal guide hole 36 and the vertical guide hole 38 have a straight line shape, respectively. The horizontal guide hole 36 extends in front and rear directions of the thigh region. Also, the horizontal guide hole 36 may be inclined upward toward a rear side of the thigh region. The vertical guide hole 38 extends in a vertical direction of the thigh region. Also, the vertical guide hole 38 may be generally vertically defined with respect to the horizontal guide hole 36. However, an angle between the horizontal guide hole 36 and the vertical guide hole 38 may be changed. Thus, a moving orbit of the connection bar 40 (or the lower trace 20) may be changed through the change of the angle between the horizontal guide hole 36 and the vertical guide hole 38.

The horizontal guide hole 36 has a preset length $d_H$. Also, the horizontal guide hole 36 has a front length less than a rear length thereof with respect to the vertical guide hole 36. Thus, the rotation of the connecting bar 40 in the front direction may be restricted. A horizontal moving body 42 is inserted into the horizontal guide hole 36 and moved along the horizontal guide hole 36. As illustrated in FIG. 5, the horizontal moving body 42 has a rectangular shape of which a length is greater than a width. Where, the width of the horizontal moving body 42 is the same as a width of the horizontal guide hole 36. Therefore, the rotation of the horizontal moving body 42 in the horizontal guide hole 36 is restricted, but the movement of the horizontal moving body 42 along the horizontal guide hole 36 is allowed. The horizontal moving body 42 is inserted through a rear surface of the guide plate 34. The guide plate 34 is coupled to the base plate 32 to prevent the horizontal moving body 42 from being separated from the horizontal guide hole 36. Specifically, the horizontal moving body 42 includes a protrusion 43. The protrusion 43 prevents the horizontal moving body 42 from being separated from the horizontal guide hole 36. The length $d_H$ of the above-described horizontal guide hole 36 may determine a movement distance of the horizontal moving body 42.

Similarly, the vertical guide hole 38 has a preset length $d_V$. A vertical moving body 44 is inserted into the vertical guide hole 38 and moved along the vertical guide hole 38. As illustrated in FIG. 5, the vertical moving body 44 has a rectangular shape of which a length is greater than a width. Where, the width of the vertical moving body 44 is the same as a width of the vertical guide hole 38. Therefore, the rotation of the vertical moving body 44 in the vertical guide hole 38 is restricted, but the movement of the vertical moving body 44 along the vertical guide hole 38 is allowed. The vertical moving body 44 is inserted through the rear surface of the guide plate 34. The guide plate 34 is coupled to the base plate 32 to prevent the vertical moving body 44 from being separated from the vertical guide hole 38. Specifically, the vertical moving body 44 includes a protrusion 45. The protrusion 45 prevents the vertical moving body 44 from being separated from the vertical guide hole 38. The length d.sub.V of the above-described vertical guide hole 38 may determine a movement distance of the vertical moving body 44.

A stopper 39 is disposed on the vertical guide hole 38 through a fixing pin P. The fixing pin P is connected to a rear end of the stopper 39 and inserted into an insertion hole 38a. Thus, the fixing pin p is fixedly disposed on the vertical guide hole 38. The stopper 39 is disposed on the vertical guide hole 38 to restrict the movement of the vertical moving body 44 and reduce the length $d_V$ of the vertical guide hole 38. This will be described later in detail.

Although the stopper is disposed on the vertical guide hole 38 in the current embodiment, the present invention is not limited thereto. For example, the stopper 39 may be disposed on the horizontal guide hole 36 or on both horizontal and vertical guide holes 36 and 38.

As described above, the connecting bar 40 has one end connected to the lower brace 20 and the other end connected to the horizontal moving body 42 and the vertical moving body 44. As shown in FIG. 2, the connecting bar 40 is rotatably connected to the horizontal moving body 42 by a coupling member 42a and rotatably connected to the vertical moving body 44 by a coupling member 44a.

Figure 6:
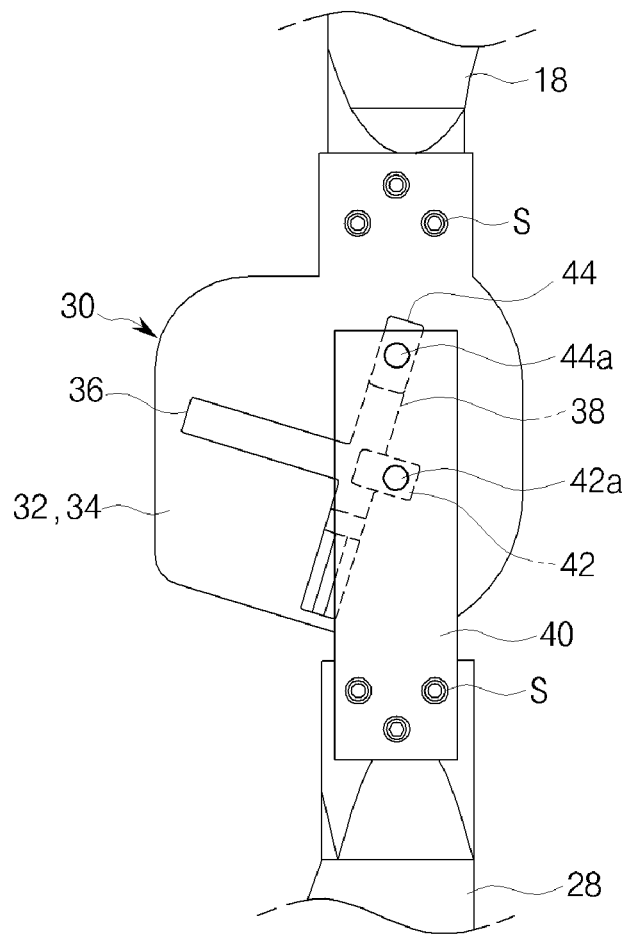
FIGS. 6 to 8 are views illustrating an operation of the reciprocal hinge shown in FIG. 5.
Figure 7:
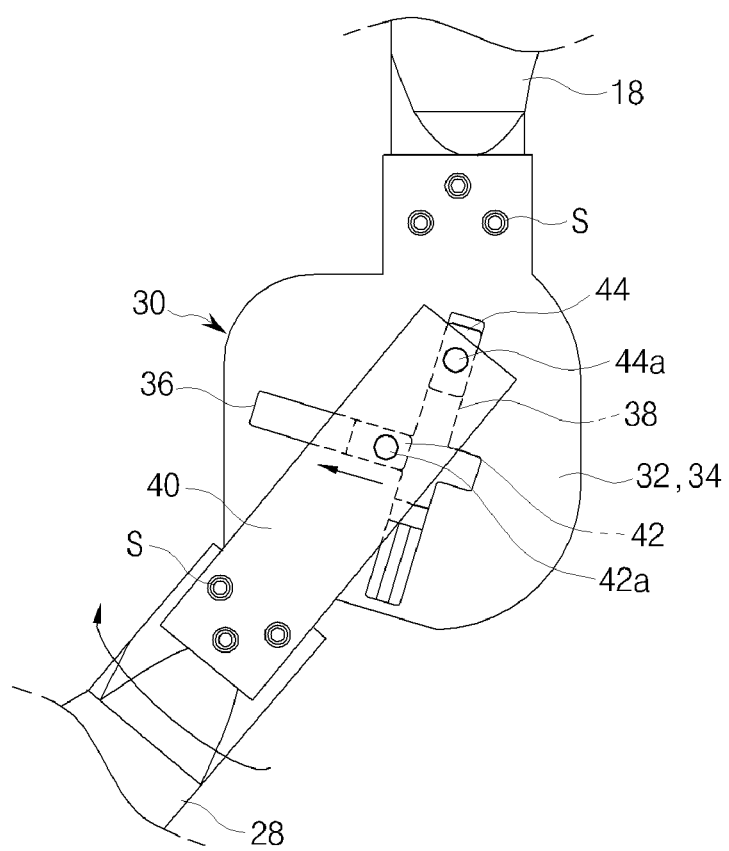
Figure 8:
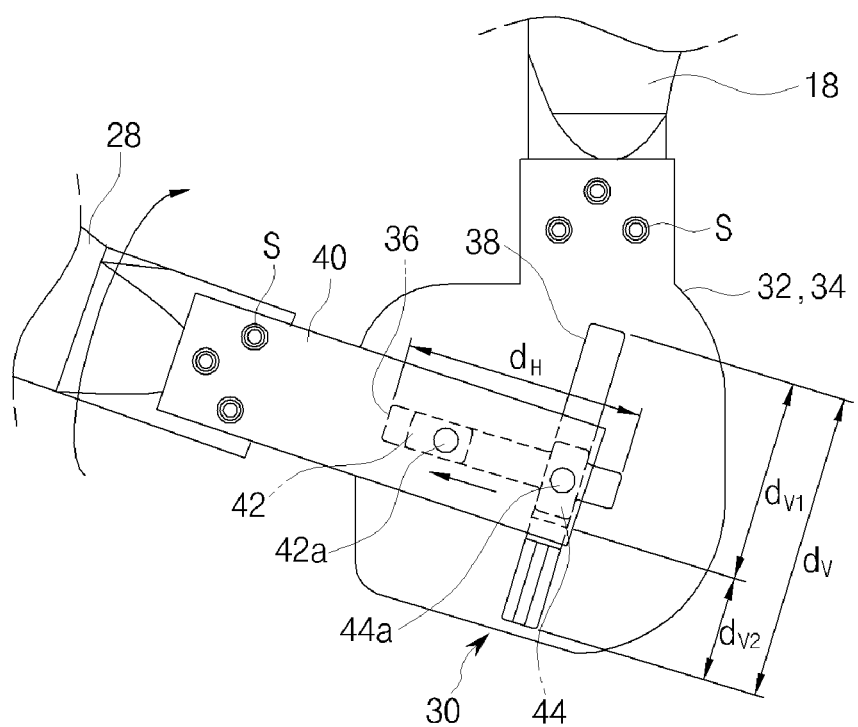

FIGS. 6 to 8 are views illustrating an operation of the reciprocal hinge shown in FIG. 5. Hereinafter, motions of the reciprocal hinge and the knee brace will be described with reference to FIGS. 6 to 8.

Referring to FIG. 6, when the upper fixing bar 18 and the lower fixing bar 28 (or the connecting bar 40) are disposed substantially parallel to each other, the horizontal moving body 42 is disposed on a right side of the horizontal guide hole 36, and the vertical moving body 44 is disposed above the vertical guide hole 38.

Referring to FIG. 7, since the connecting bar 40 is rotated with respect to the guide plate 34, the horizontal moving body 42 is moved in a left direction, and the vertical moving body 44 is moved downward. The connecting bar 40 is connected to the horizontal moving body 42 and the vertical moving body 44 by the coupling members 42a and 44a. Also, the connecting bar 40 is rotated with respect to the horizontal moving body 42 and the vertical moving body 44 through the coupling members 42a and 44a.

Referring to FIG. 8, the more the connecting bar 40 is rotated, the more the horizontal moving body 42 is moved in the left direction. Then, the connecting bar 40 is rotated until the horizontal moving body 42 reaches a left end of the horizontal guide hole 36 and the vertical moving body 44 reaches a lower end of the vertical guide hole 38. Here, the stopper 39 is disposed on the vertical guide hole 38 to reduce a length of the vertical guide hole ($d_V - d_{V2} = d_{V1}$) and restrict the movement of the vertical moving body 44. Thus, a rotation angle of the connecting bar 40 is reduced by the stopper 39. Here, the fixing pin P disposed on the rear end of the stopper 39 may be replaced with a damper (e.g., an elastic body). The damper may absorb an impact applied to the stopper 39.

Here, unlike the current embodiment, as the connecting bar 40 is rotated, the horizontal moving body 42 and the vertical moving body 44 may be moved along the horizontal guide hole 36 and the vertical guide hole 38 to allow the connecting bar 40 to be rotated. Specifically, the guide plate 34 may be rotated with respect to the base plate 32. Since the guide plate 34 is rotated, the rotation movement of the connecting bar 40 may be variously changed.

Figure 9:
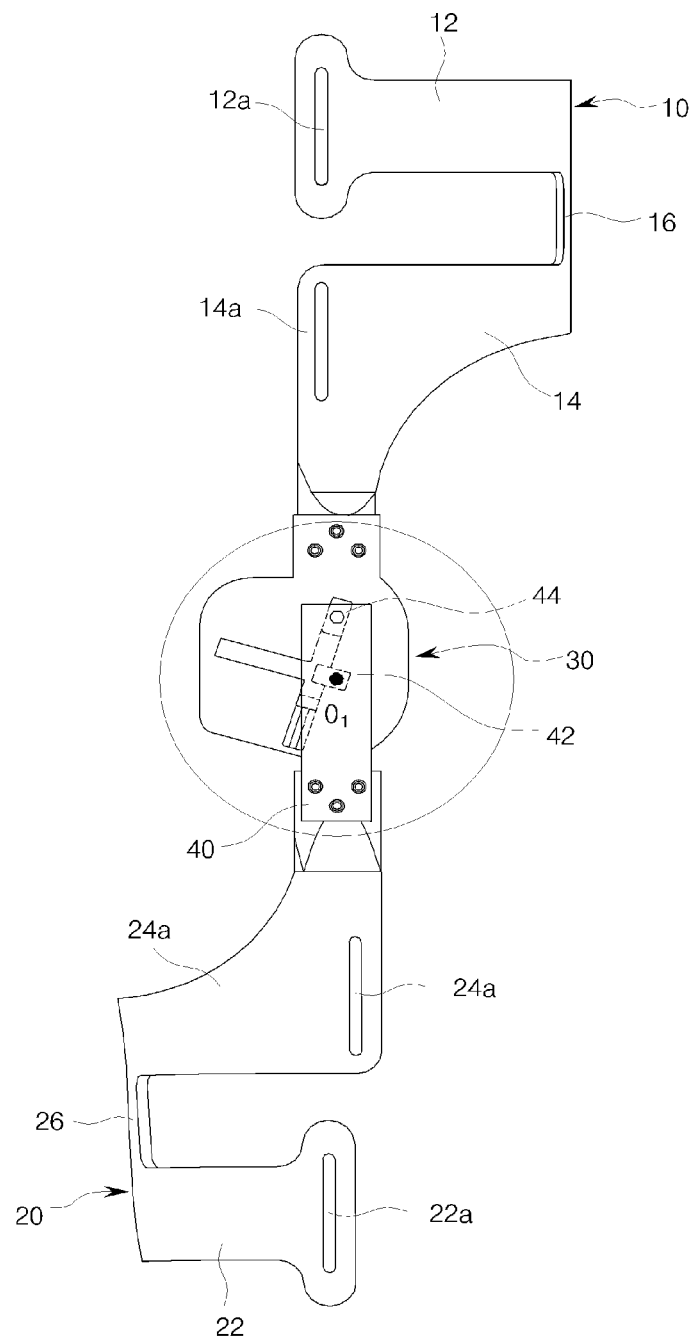
FIGS. 9 to 11 are views illustrating a motion of the knee brace shown in FIG. 2.
Figure 10:
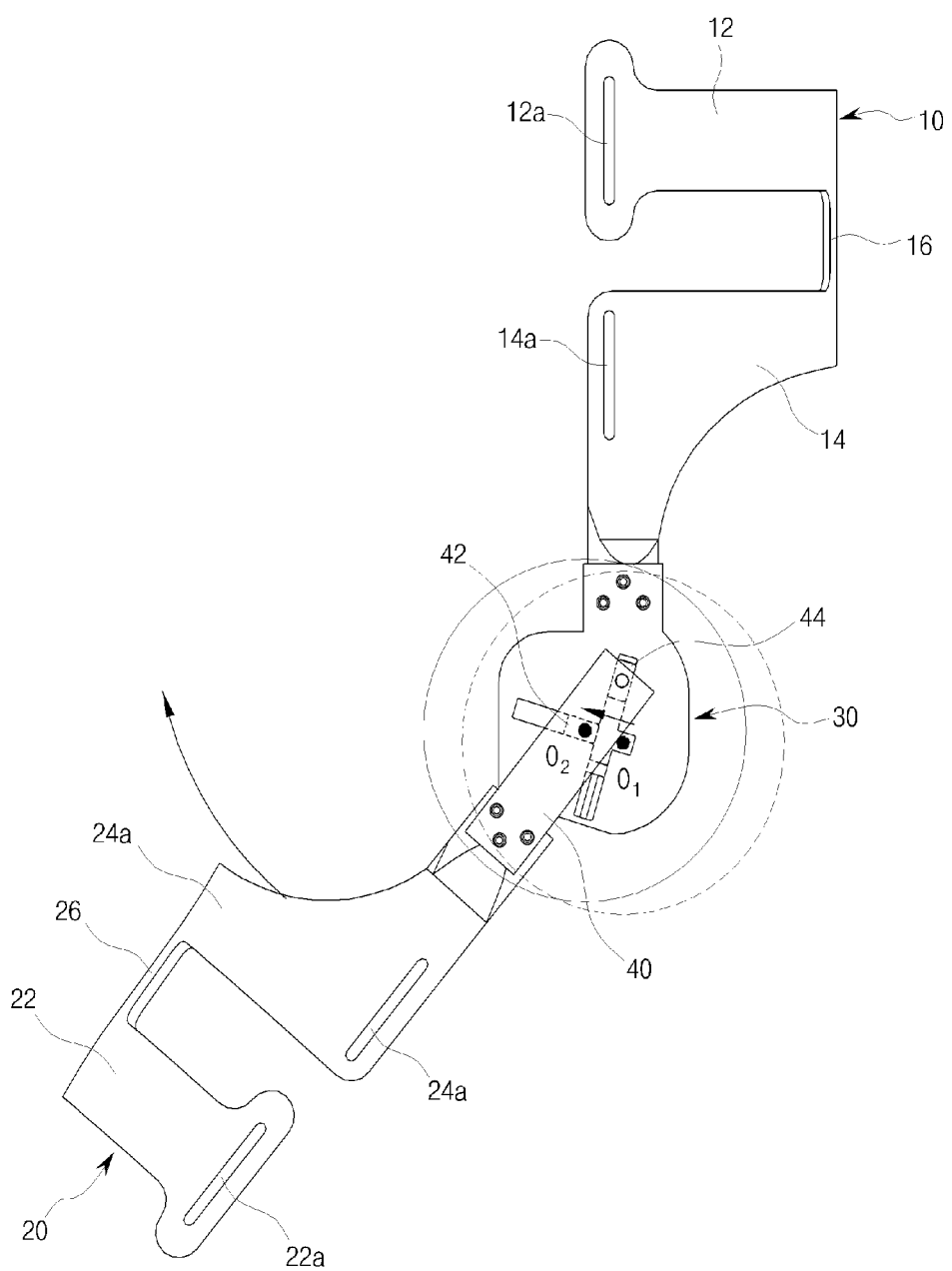
Figure 11:
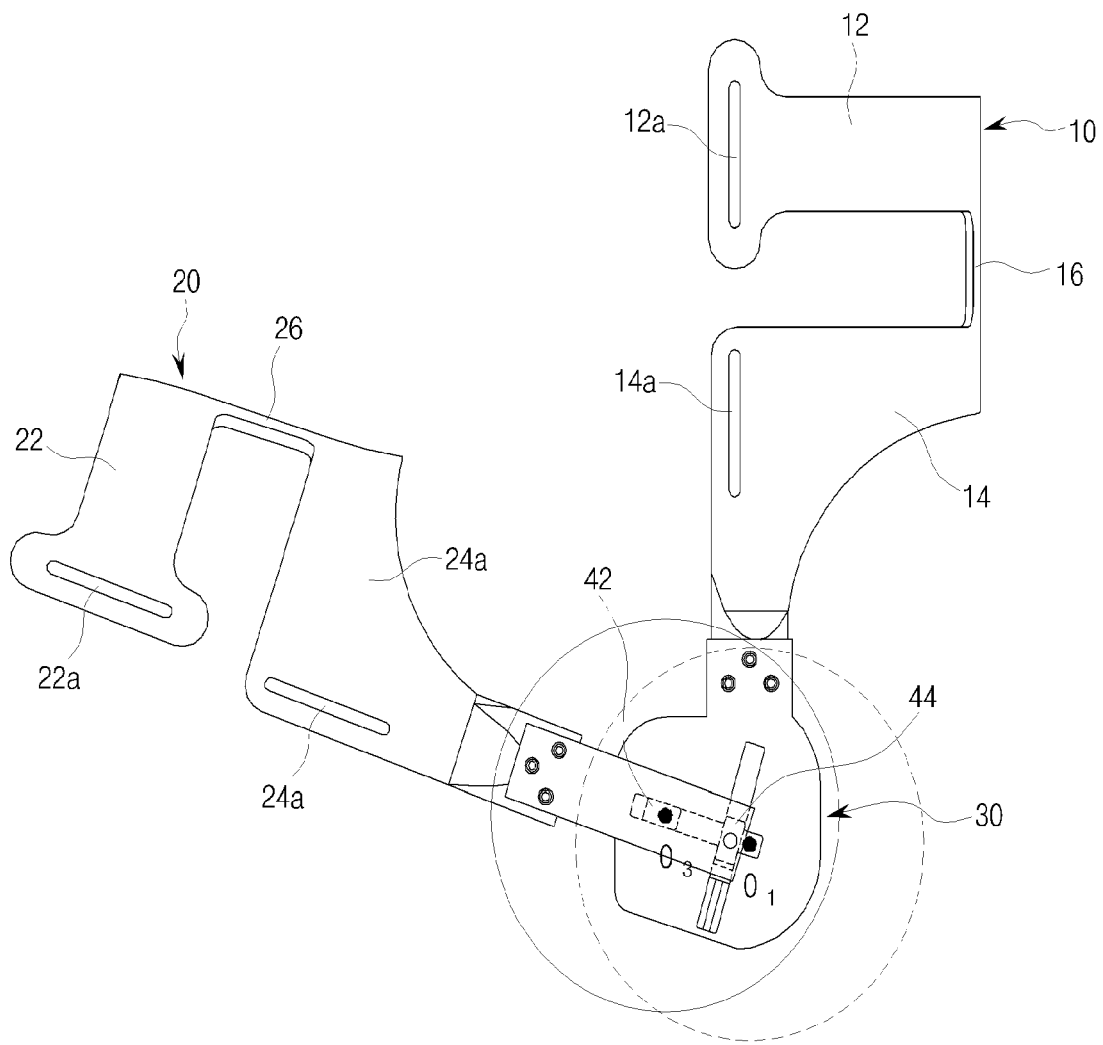

FIGS. 9 to 11 are views illustrating a motion of the knee brace shown in FIG. 2. Referring to FIGS. 9 to 11, the rotation of the connecting bar 40 denotes the rotation of the lower brace 20. As the horizontal moving body 42 and the vertical moving body 44 are moved, the lower brace 20 is rotated together with the connecting bar 40.

Here, as shown in FIGS. 10 and 11, the connecting bar 40 is rotated along an elliptical orbit (according to a trace of the lower end of the connecting bar 40), a rotation center of the connecting bar 40 is moved together with the movement of the horizontal moving body 42 ($O_1 \rightarrow O_2 \rightarrow O_3$). Thus, it may be seen that the motion of the reciprocal hinge is similar to that of the knee joint, i.e., the rotation movement of the upper end of the shinbone along the elliptical orbit with respect to the lower end of the thighbone and the movement of the rotation center of the upper end of the shinbone. Thus, the motion of the knee trace may be realized similar to the motion of the knee joint through the above-described methods.

Although the present invention is described in more detail with reference to the preferred embodiment, the present invention is not limited thereto. For example, various embodiments may be applied to the present invention. Thus, technical idea and scope of claims set forth below are not limited to the preferred embodiments.

INDUSTRIAL APPLICABILITY

According to the current embodiments, it may prevent the knee joint of the wearer from being collaterally injured. For this, the knee brace may be equivalent or optimized with respect to the left and right knee joints as well as may be modified according to the trace of the knee joint of the wearer. Also, the knee brace may be applied to animals in addition to persons.

What is claimed is:

1. A knee brace comprising:
an upper brace disposed to correspond to a thigh region of a wearer when the knee brace is worn;
a lower brace disposed to correspond to a shin region of the wearer when the knee brace is worn; and
a reciprocal hinge connecting the upper brace to the lower brace such that the lower brace is relatively rotated with respect to the upper brace, the reciprocal hinge including
a guide plate connected to the upper brace and having first and second guide holes, both of the first and second guide holes having a straight line shape and crossing each other with a preset angle,
first and second moving bodies respectively sliding along the first and second guide holes of the guide plate and having first and second coupling members integral with a surface of the moving bodies, and
a connecting bar of which one side is connected to the lower brace and the other side is rotatably coupled with the first and second moving bodies by the first and second coupling members respectively, the connecting bar being rotated with respect to the guide plate as the first and second moving bodies slide along the first and second guide holes respectively,
wherein the first moving body has a rectangular shape of which a width is the same as a width of the first guide hole and a length is greater than the width of the first moving body, and the second moving body has a rectangular shape of which a width is the same as a width of the second guide hole and a length is greater than the width of the second moving body.

2. The knee brace of claim 1, wherein the first and second guide holes are perpendicular to each other.

3. The knee brace of claim 1, wherein the one end of the connecting bar is rotated along an elliptical orbit when the connection bar is rotated.

4. The knee brace of claim 1, wherein the reciprocal hinge has a rotation angle, and the rotation angle is an angle defined by the connecting bar when the first moving body is disposed on one end of the guide hole and the second moving body is disposed on one end of the second guide hole and when the connecting bar and the first moving body are disposed on the other end of the first guide hole and the second moving body is disposed on the other end of the second guide hole.

5. The knee brace of claim 4, wherein the reciprocal hinge further comprises a stopper inserted into one of the first and the second guide holes to restrict the movement of one of the first and second moving bodies.

6. The knee brace of claim 5, wherein the reciprocal hinge further comprises a damper connected to a rear end of the stopper to absorb an impact applied to the stopper.

7. A knee brace comprising:
an upper brace disposed to correspond to a thigh region of a wearer when the knee brace is worn;
a lower brace disposed to correspond to a shin region of the wearer when the knee brace is worn; and
a reciprocal hinge connecting the upper brace to the lower brace such that the lower brace is relatively rotated with respect to the upper brace, the reciprocal hinge including
a guide plate connected to the upper brace and having first and second guide holes, both of the first and second guide holes having a straight line shape and crossing each other with a preset angle,
first and second moving bodies respectively sliding along the first and second guide holes of the guide plate and having first and second coupling members integral with a surface of the moving bodies, and
a connecting bar of which one side is connected to the lower brace and the other side is rotatably coupled with the first and second moving bodies by the first and second coupling members respectively, the connecting bar being rotated with respect to the guide plate as the first and second moving bodies slide along the first and second guide holes respectively,
wherein the first moving body has a rectangular shape of which a width is the same as a width of the first guide hole and a length is greater than the width of the first moving body, and the second moving body has a rectangular shape of which a width is the same as a width of the second guide hole and a length is greater than the width of the second moving body,
wherein the first guide hole extends in front and rear directions of the thigh region and is inclined upward toward a rear side, and the second guide hole extends in a vertical direction of the thigh region and is substantially perpendicular to the first guide hole, and
wherein the first moving body is disposed on the lower end of the first guide hole when the connecting bar is a vertical condition.

8. The knee brace of claim 7, wherein the first guide hole has a first front guide hole defined in a front side of the second guide hole and a first rear guide hole defined in a rear side of the second guide hole, and the first front guide hole has a length less than that of the first rear guide hole.

* * * * *